(12) United States Patent
Tsay et al.

(10) Patent No.: US 11,466,321 B2
(45) Date of Patent: Oct. 11, 2022

(54) ARRAY INCLUDING SEQUENCING PRIMER AND NON-SEQUENCING ENTITY

(71) Applicant: ILLUMINA, INC., San Diego, CA (US)

(72) Inventors: James Tsay, San Diego, CA (US); Yuxiang Huang, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 530 days.

(21) Appl. No.: 16/471,411

(22) PCT Filed: Dec. 20, 2017

(86) PCT No.: PCT/US2017/067566
§ 371 (c)(1),
(2) Date: Jun. 19, 2019

(87) PCT Pub. No.: WO2018/119057
PCT Pub. Date: Jun. 28, 2018

(65) Prior Publication Data
US 2020/0190575 A1    Jun. 18, 2020

Related U.S. Application Data

(60) Provisional application No. 62/438,294, filed on Dec. 22, 2016.

(51) Int. Cl.
*C12Q 1/6874*    (2018.01)
*B01L 3/00*    (2006.01)
*C40B 40/06*    (2006.01)

(52) U.S. Cl.
CPC ......... *C12Q 1/6874* (2013.01); *B01L 3/5085* (2013.01); *B01L 2300/069* (2013.01); *B01L 2300/0819* (2013.01); *B01L 2300/0896* (2013.01); *B01L 2300/12* (2013.01); *C40B 40/06* (2013.01)

(58) Field of Classification Search
None
See application file for complete search history.

(56) References Cited

U.S. PATENT DOCUMENTS

| | | | |
|---|---|---|---|
| 2003/0099964 A1 | 5/2003 | Patil et al. | |
| 2009/0118128 A1* | 5/2009 | Liu et al. | C12Q 1/6806 506/26 |

(Continued)

FOREIGN PATENT DOCUMENTS

| | | |
|---|---|---|
| CN | 104968427 A | 10/2015 |
| CN | 105874385 A | 8/2016 |

(Continued)

OTHER PUBLICATIONS

Chuan, Wang, et al., "Techniques for Detection in Molecular Biology", Sichuan University Press, Jul. 31, 2016, 5 pages.

(Continued)

*Primary Examiner* — Kaijiang Zhang
(74) *Attorney, Agent, or Firm* — Illumina, Inc.

(57) ABSTRACT

An example of an array includes a support including a plurality of discrete wells, a gel material positioned in each of the discrete wells, a sequencing primer grafted to the gel material, and a non-sequencing entity grafted to the gel material. Each of the sequencing primer and the non-sequencing entity is in its as-grafted form.

23 Claims, 7 Drawing Sheets

Specification includes a Sequence Listing.

(56) References Cited

U.S. PATENT DOCUMENTS

| | | |
|---|---|---|
| 2011/0059865 A1 | 3/2011 | Smith et al. |
| 2013/0116153 A1* | 5/2013 | Bowen et al. .......... C40B 50/18 506/26 |
| 2015/0000544 A1 | 1/2015 | Berti et al. |
| 2015/0005447 A1 | 1/2015 | Berti et al. |
| 2015/0087534 A1 | 3/2015 | Gormley et al. |
| 2015/0299784 A1 | 10/2015 | Fan |
| 2016/0040225 A1 | 2/2016 | Wu et al. |
| 2016/0256846 A1 | 9/2016 | Smith et al. |

FOREIGN PATENT DOCUMENTS

| | | |
|---|---|---|
| RU | 2270254 C2 | 2/2006 |
| WO | 2003/049677 A2 | 6/2003 |
| WO | 2013/063382 A2 | 5/2013 |
| WO | 2013063382 A2 | 5/2013 |
| WO | 2014/133905 | 9/2014 |
| WO | 2016/040607 A1 | 3/2016 |

OTHER PUBLICATIONS

Shchepinov, et al., "Steric factors influencing hybridisation of nucleic acids to oligonucleotide arrays", Nucl. Acids Res,. vol. 25, No. 6, 1997, pp. 1155-1161.

Altman, et al., "Cyanine Fluorophore Derivatives with Enhanced Photostability", Nat Methods. 9(1), 2012, 68-71.

* cited by examiner

ARRAY INCLUDING SEQUENCING PRIMER AND NON-SEQUENCING ENTITY

CROSS-REFERENCE TO RELATED APPLICATIONS

This application is a 35 U.S.C. § 371 National Stage application of International Patent Application No. PCT/US2017/067566, filed on Dec. 20, 2017, which claims the benefit of U.S. Provisional Application Ser. No. 62/438,294, filed Dec. 22, 2016, the contents of which is incorporated by reference herein in its entirety.

REFERENCE TO SEQUENCE LISTING

The Sequence Listing submitted herewith via EFS-Web is hereby incorporated by reference in its entirety. The name of the file is ILI102BPCT_IP-1486-PCT_sequence_listing_ST25.txt, the size of the file is 647 bytes, and the date of creation of the file is Dec. 20, 2017.

BACKGROUND

Biological arrays are among a wide range of tools used to detect and analyze molecules, including deoxyribonucleic acid (DNA) and ribonucleic acid (RNA). In these applications, the arrays are engineered to include probes for nucleotide sequences present in genes in humans and other organisms. In certain applications, for example, individual DNA and RNA probes may be attached at small locations in a geometric grid (or randomly) on an array support. A test sample, e.g., from a known person or organism, may be exposed to the grid, such that complementary fragments hybridize to the probes at the individual sites in the array. The array can then be examined by scanning specific frequencies of light over the sites to identify which fragments are present in the sample, by fluorescence of the sites at which the fragments hybridized.

Biological arrays may be used for genetic sequencing. In general, genetic sequencing involves determining the order of nucleotides or nucleic acids in a length of genetic material, such as a fragment of DNA or RNA. Increasingly longer sequences of base pairs are being analyzed, and the resulting sequence information may be used in various bioinformatics methods to logically fit fragments together so as to reliably determine the sequence of extensive lengths of genetic material from which the fragments were derived. Automated, computer-based examination of characteristic fragments have been developed, and have been used in genome mapping, identification of genes and their function, evaluation of risks of certain conditions and disease states, and so forth. Beyond these applications, biological arrays may be used for the detection and evaluation of a wide range of molecules, families of molecules, genetic expression levels, single nucleotide polymorphisms, and genotyping.

SUMMARY

An example of an array includes a support including a plurality of discrete wells, a gel material positioned in each of the discrete wells, a sequencing primer grafted to the gel material, and a non-sequencing entity grafted to the gel material. Each of the sequencing primer and the non-sequencing entity is in its as-grafted form.

Another example of the array includes a support including a plurality of discrete wells, a gel material positioned in each of the discrete wells, a sequencing primer grafted to the gel material, and a spacer grafted to the gel material. The spacer is selected from the group consisting of a dendrimer, polydextran, methacryloyloxyethyl phosphorylcholine, poly(ethylene glycol), poly(ethylene imine), poly-L-lysine, propargyl methacrylate, poly(methyl methacrylate), poly(N-isopropylacrylamide), poly(ethylene glycol) acrylate, poly(propylene imine), poly(vinyl alcohol), poly(2-ethyl-2-oxazoline), polyacrylic acid, poly(trolox ester), and combinations thereof.

In an example of a method, a gel is positioned in each of a plurality of discrete wells of a support, a sequencing primer is grafted to the gel material; and a non-sequencing entity is grafted to the gel material.

BRIEF DESCRIPTION OF THE DRAWINGS

Features and advantages of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

INTRODUCTION

Figure 1:
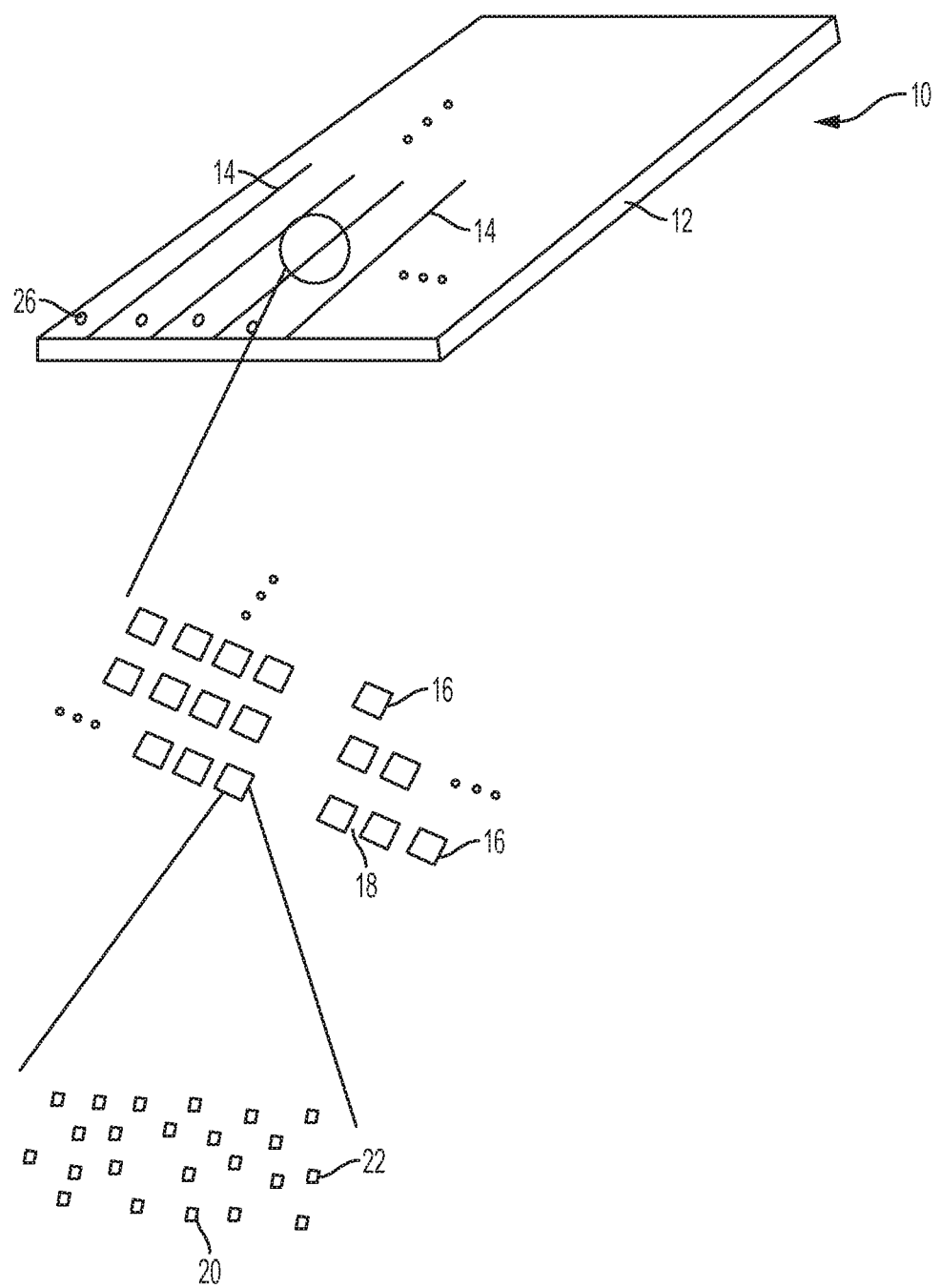
FIG. 1 is a diagrammatical representation of an example array according to the present disclosure, illustrating the overall layout of the array and detailing the arrangement of individual sites.

In a first aspect of the array disclosed herein, the array comprises a support including a plurality of discrete wells, a gel material positioned in each of the discrete wells, a sequencing primer grafted to the gel material, and a non-sequencing entity grafted to the gel material, each of the sequencing primer and the non-sequencing entity being in its as-grafted form.

In the first aspect of the array, a molar ratio of the non-sequencing entity to the sequencing primer ranges from about 0.25:1 to about 5:1.

In one example of the first aspect of the array, the non-sequencing entity is selected from the group consisting of a dendrimer, polydextran, methacryloyloxyethyl phosphorylcholine, poly(ethylene glycol), poly(ethylene imine), poly-L-lysine, propargyl methacrylate, poly(methyl methacrylate), poly(N-isopropylacrylamide), poly(ethylene glycol) acrylate, poly(propylene imine), poly(vinyl alcohol), poly(2-ethyl-2-oxazoline), polyacrylic acid, poly(trolox ester), a peptide, and a non-functional primer. The non-sequencing entity is grafted to the gel material through a terminal functional group. In some examples, the functional group is selected from the group consisting of an alkyne, a norbornyl, a copper free click moiety, and a thiol. As an example in this first aspect, the non-sequencing entity is the non-functional primer, and the non-functional primer is polyT or polyA. As another example in this first aspect, the non-sequencing entity is poly(ethylene glycol) having a molecular weight ranging from about 0.5 KDa to less than about 10 KDa.

In another example of the first aspect of the array, the non-sequencing entity includes a linker and a triplet state quencher or an anti-oxidant bound to the linker. In some examples, the linker is selected from the group consisting of a dendrimer, polydextran, methacryloyloxyethyl phosphorylcholine, poly(ethylene glycol), poly(ethylene imine), poly-L-lysine, propargyl methacrylate, poly(methyl methacrylate), poly(N-isopropylacrylamide), poly(ethylene glycol) acrylate, poly(propylene imine), poly(vinyl alcohol), poly(2-ethyl-2-oxazoline), polyacrylic acid, and poly(trolox ester). In some examples of this aspect, the triplet state quencher is selected from the group consisting of cyclo-octyltetraene (COT), Trolox, and nitrobenzyl alcohol (NBA); and in some examples, the anti-oxidant is selected from the group consisting of ascorbate, glutathione, gallic acid, catechin, Trolox, and vitamin E.

In still another example of the first aspect of the array, the non-sequencing entity includes a linker and a fluorescence resonance energy transfer (FRET) donor bound to the linker. In some examples, the linker is selected from the group consisting of a dendrimer, polydextran, methacryloyloxyethyl phosphorylcholine, poly(ethylene glycol), poly(ethylene imine), poly-L-lysine, propargyl methacrylate, poly(methyl methacrylate), poly(ethylene glycol) acrylate, poly(propylene imine), poly(vinyl alcohol), poly(2-ethyl-2-oxazoline), polyacrylic acid, and poly(trolox ester). In some examples of this aspect, the FRET donor is selected from the group consisting of a donor dye to FRET with a green-emitting dye and a donor dye to FRET with a red-emitting dye.

It is to be understood that any features of the first aspect of the array may be combined together in any desirable manner and/or configuration.

In a second aspect of the array disclosed herein, the array comprises a support including a plurality of discrete wells, a gel material positioned in each of the discrete wells, a sequencing primer grafted to the gel material, and a spacer grafted to the gel material. In some examples, the spacer being selected from the group consisting of a dendrimer, polydextran, methacryloyloxyethyl phosphorylcholine, poly (ethylene glycol), poly(ethylene imine), poly-L-lysine, propargyl methacrylate, poly(methyl methacrylate), poly (ethylene glycol) acrylate, poly(propylene imine), poly(vinyl alcohol), poly(2-ethyl-2-oxazoline), polyacrylic acid, poly(trolox ester), and combinations thereof.

In the second aspect of the array 10, a molar ratio of the spacer to the sequencing primer ranges from about 0.25:1 to about 5:1.

One example of the second aspect of the array further comprises a triplet state quencher, an anti-oxidant, or a fluorescence resonance energy transfer (FRET) donor bound to the spacer. In some examples of this aspect, the triplet state quencher is selected from the group consisting of cyclo-octyltetraene (COT), Trolox, and nitrobenzyl alcohol (NBA). In some examples of this aspect, the anti-oxidant is selected from the group consisting of ascorbate, glutathione, gallic acid, catechin, Trolox, and vitamin E. In some examples of this aspect, the FRET donor is selected from the group consisting of a donor dye to FRET with a green-emitting dye and a donor dye to FRET with a red-emitting dye.

In one example of the second aspect of the array, the spacer is grafted to the gel material through a terminal functional group. In some examples, the functional group is selected from the group consisting of an alkyne, a norbornyl, a copper free click moiety, and a thiol.

It is to be understood that any features of the second aspect of the array may be combined together in any desirable manner. Moreover, it is to be understood that any combination of features of the first aspect and/or second aspect may be used together, and/or that any features from either or both of these aspects may be combined with any of the examples disclosed herein.

An aspect of the method comprises positioning a gel material in each of a plurality of discrete wells of a support, grafting a sequencing primer to the gel material, and grafting a non-sequencing entity to the gel material.

In one example of this aspect of the method, the sequencing primer is grafted to the gel material before or after the non-sequencing entity is grafted to the gel material.

In another example of this aspect of the method, the sequencing primer and the non-sequencing entity are co-grafted to the gel material. Co-grafting is accomplished by depositing a mixture of the sequencing primer and the non-sequencing entity onto the support having the gel material thereon; and incubating the support at a predetermined temperature.

In this aspect of the method, the non-sequencing entity is selected from the group consisting of a dendrimer, polydextran, methacryloyloxyethyl phosphorylcholine, poly(ethylene glycol), poly(ethylene imine), poly-L-lysine, propargyl methacrylate, poly(methyl methacrylate), poly(ethylene glycol) acrylate, poly(propylene imine), poly(vinyl alcohol), poly(2-ethyl-2-oxazoline), polyacrylic acid, poly(trolox ester), a peptide, and a non-functional primer; and the non-sequencing entity is grafted to the gel material through a terminal functional group. In some examples, the terminal functional group is selected from the group consisting of an alkyne, a norbornyl, a copper free click moiety, and a thiol.

In some aspects of the method, the non-sequencing entity further comprises a comprises a triplet state quencher, an anti-oxidant, or a fluorescence resonance energy transfer (FRET) donor bound thereto.

It is to be understood that any features of this aspect of the method may be combined together in any desirable manner. Moreover, it is to be understood that any combination of features of this aspect of the method may be combined with any of the aspects of the array and/or any of the examples disclosed herein.

DETAILED DESCRIPTION

Examples of the arrays disclosed herein include several sites, each of which has the sequencing primer and the non-sequencing entity attached to the gel material. The sequencing primer may be used in binding and amplifying deoxyribonucleic acids (DNA) or ribonucleic acids (RNA), while the non-sequencing entity does not participate in binding or amplifying. Rather, the non-sequencing entity acts as a spacer between sequencing primers. Spacing out the sequencing primers may enhance amplification by limiting steric hindrance for proteins involved in the amplification process.

In addition to acting as a spacer, the non-sequencing entity may also introduce other functionalities to the array. As examples, the non-sequencing entity may i) limit the non-specific binding of enzymes, proteins, and/or other small molecules to the gel material during amplification and sequencing; ii) increase the hydrophilicity of the gel material, which can help prevent its collapse under dry conditions; iii) enhance fluorescence properties of dyes linked to the gel material; and/or iv) combinations of i, ii, and/or iii. Still further, the non-sequencing entity may aid in exposing the functional surface primers from the surface.

It is to be understood that terms used herein will take on their ordinary meaning in the relevant art unless specified otherwise. Several terms used herein and their meanings are set forth below.

The singular forms "a", "an", and "the" include plural referents unless the context clearly dictates otherwise.

As used herein, "alkyl" refers to a straight or branched hydrocarbon chain that is fully saturated (i.e., contains no double or triple bonds). The alkyl group may have 1 to 20 carbon atoms. Example alkyl groups include methyl, ethyl, propyl, isopropyl, butyl, isobutyl, tertiary butyl, pentyl, hexyl, and the like. As an example, the designation "C1-4 alkyl" indicates that there are one to four carbon atoms in the alkyl chain, i.e., the alkyl chain is selected from the group consisting of methyl, ethyl, propyl, iso-propyl, n-butyl, isobutyl, sec-butyl, and t-butyl.

As used herein, "alkenyl" refers to a straight or branched hydrocarbon chain containing one or more double bonds. The alkenyl group may have 2 to 20 carbon atoms. Example alkenyl groups include ethenyl, propenyl, butenyl, pentenyl, hexenyl, and the like. The alkenyl group may be designated as, for example, "C2-4 alkenyl," which indicates that there are two to four carbon atoms in the alkenyl chain.

As used herein, "alkynyl" refers to a straight or branched hydrocarbon chain containing one or more triple bonds. The alkynyl group may have 2 to 20 carbon atoms. The alkynyl group may be designated, for example, as "C2-4 alkynyl," which indicates that there are two to four carbon atoms in the alkynyl chain.

An "amino" functional group refers to an —$NR_aR_b$ group, where $R_a$ and $R_b$ are each independently selected from hydrogen, C1-6 alkyl, C2-6 alkenyl, C2-6 alkynyl, C3-7 carbocyclyl, C6-10 aryl, 5-10 membered heteroaryl, and 5-10 membered heterocyclyl, as defined herein.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, which may be designated as C6-18. Examples of aryl groups include phenyl, naphthyl, azulenyl, and anthracenyl.

The phrase "as-grafted form" refers to the state of a primer and/or non-sequencing entity as it is attached to the gel material as a result of grafting, and without any alteration. In the examples disclosed herein, the non-sequencing entity in its as-grafted form is not capable of undergoing DNA or RNA sequencing. In other words, from the point at which the non-sequencing entity is grafted to the gel material, it is not able to be sequenced. As such, additional processing steps do not have to be taken in order to render the non-sequencing entity non-reactive during sequencing. Rather, when the non-sequencing entity is grafted, it is not able to be sequenced.

As used herein, the term "attached" refers to the state of two things being joined, fastened, adhered, connected, or bound to each other. For example, a nucleic acid can be attached to a material, such as the gel material, by a covalent or non-covalent bond. A covalent bond is characterized by the sharing of pairs of electrons between atoms. A non-covalent bond is a chemical bond that does not involve the sharing of pairs of electrons and can include, for example, hydrogen bonds, ionic bonds, van der Waals forces, hydrophilic interactions and hydrophobic interactions.

An "azide" or "azido" functional group refers to —$N_3$.

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation, provided that at least one ring in a ring system is not aromatic. Thus, carbocyclyls include cycloalkyls, cycloalkenyls, and cycloalkynyls. The carbocyclyl group may have 3 to 20 carbon atoms (i.e., C3-20). Examples of carbocyclyl rings include cyclopropyl, cyclobutyl, cyclopentyl, cyclohexyl, cyclohexenyl, 2,3-dihydro-indene, bicyclo[2.2.2]octanyl, adamantyl, and spiro[4.4]nonanyl.

As used herein, the term "carboxylic acid" or "carboxyl" as used herein refers to —C(O)OH.

As used herein, "cycloalkyl" means a fully saturated carbocyclyl ring or ring system. Examples include cyclopropyl, cyclobutyl, cyclopentyl, and cyclohexyl.

As used herein, "cycloalkylene" means a fully saturated carbocyclyl ring or ring system that is attached to the rest of the molecule via two points of attachment.

As used herein, "cycloalkenyl" or "cycloalkane" means a carbocyclyl ring or ring system having at least one double bond, wherein no ring in the ring system is aromatic. Examples include cyclohexenyl or cyclohexene and norbornene or norbornenyl. Also as used herein, "heterocycloalkenyl" or "heterocycloalkene" means a carbocyclyl ring or ring system with at least one heteroatom in ring backbone, having at least one double bond, wherein no ring in the ring system is aromatic.

As used herein, "cycloalkynyl" or "cycloalkyne" means a carbocyclyl ring or ring system having at least one triple bond, wherein no ring in the ring system is aromatic. An example is cyclooctyne. Another example is bicyclononyne. Also as used herein, "heterocycloalkynyl" or "heterocycloalkyne" means a carbocyclyl ring or ring system with at least one heteroatom in ring backbone, having at least one triple bond, wherein no ring in the ring system is aromatic.

The term "depositing," as used herein, refers to any suitable application technique, which may be manual or automated. Generally, depositing may be performed using vapor deposition techniques, coating techniques, grafting techniques, or the like. Some specific examples include chemical vapor deposition (CVD), spray coating, spin coating, dunk or dip coating, puddle dispensing, or the like.

The term "each," when used in reference to a collection of items, is intended to identify an individual item in the collection but does not necessarily refer to every item in the collection. Exceptions can occur if explicit disclosure or context clearly dictates otherwise.

The "fluorescence enhancer" is any molecule that can improve a property of fluorescence or that can decrease photo-induced damage. For example, the fluorescence enhancer may be an anti-oxidant that improves the photo-stability of a fluorescence dye (or fully functional nucleotide (FFN) incorporated in the sequencing by synthesis (SBS)

process). For another example, the fluorescence enhancer may be a fluorescence resonance energy transfer (FRET) donor, which absorbs energy in one region of the absorption spectrum and donates energy to excite dyes (e.g., which may be attached to nucleotide(s)) in another region. The FRET donor may be a donor dye to FRET with the dye incorporated and detected in a sequencing by synthesis (SBS) workflow. For still another example, the fluorescence enhancer may be a triplet state quencher that can mitigate photo-induced damage (e.g., to nucleic acids) that may be caused by highly reactive triplet-state fluorophores. The triplet state quencher may shorten the lifetime of an excited compound in a triplet state, thereby reducing the amount of time the triplet-state compound can cause photo-induced damage to another component attached to the gel material.

As used herein, the term "gel material" is intended to mean a semi-rigid material that is permeable to liquids and gases. Typically, the gel material is a hydrogel that can swell when liquid is taken up and can contract when liquid is removed by drying.

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. In the ring system, the heteroatom(s) may be present in either a non-aromatic or aromatic ring. The heterocyclyl group may have 3 to 20 ring members (i.e., the number of atoms making up the ring backbone, including carbon atoms and heteroatoms). The heterocyclyl group may be designated as "3-6 membered heterocyclyl" or similar designations. In some examples, the heteroatom(s) are O, N, or S.

The term "hydrazine" or "hydrazinyl" as used herein refers to a —NHNH$_2$ group.

As used herein, the term "hydrazone" or "hydrazonyl" as used herein refers to a

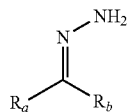

group in which R$_a$ and R$_b$ are previously defined herein.

As used herein, "hydroxyl" is an —OH group.

As used herein, the term "interstitial region" refers to an area in a substrate/support or on a surface that separates other areas of the substrate or surface. For example, an interstitial region can separate one feature of an array from another feature of the array. The two features that are separated from each other can be discrete, i.e., lacking contact with each other. In another example, an interstitial region can separate a first portion of a feature from a second portion of a feature. In many examples, the interstitial region is continuous whereas the features are discrete, for example, as is the case for a plurality of wells defined in an otherwise continuous surface. The separation provided by an interstitial region can be partial or full separation. Interstitial regions may have a surface material that differs from the surface material of the features defined in the surface. For example, features of an array can have an amount or concentration of gel material, sequencing primer(s), and non-sequencing entities that exceeds the amount or concentration present at the interstitial regions. In some examples, gel material, sequencing primer(s), and non-sequencing entities may not be present at the interstitial regions.

"Nitrile oxide," as used herein, means a "R$_a$C≡N$^+$O$^-$" group in which R$_a$ is previously defined herein. Examples of preparing nitrile oxide include in situ generation from aldoximes by treatment with chloramide-T or through action of base on imidoyl chlorides [RC(Cl)=NOH].

"Nitrone," as used herein, means a "R$_a$R$_b$C=NR$_c$$^+$O$^-$" group in which R$_a$ and R$_b$ are previously defined herein and R$_c$ is selected from C1-6 alkyl, C2-6 alkenyl, C2-6 alkynyl, C3-7 carbocyclyl, C6-10 aryl, 5-10 membered heteroaryl, and 5-10 membered heterocyclyl, as defined herein.

As used herein, a "nucleotide" includes a nitrogen containing heterocyclic base, a sugar, and one or more phosphate groups. Nucleotides are monomeric units of a nucleic acid sequence. In RNA, the sugar is a ribose, and in DNA a deoxyribose, i.e., a sugar lacking a hydroxyl group that is present at the 2' position in ribose. The nitrogen containing heterocyclic base can be a purine base or a pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine.

The "non-sequencing entity" referred to herein may be any spectator molecule that does not actively participate in DNA or RNA synthesis. The non-sequencing entity may be used to provide spacing between the grafted sequencing primers. The non-sequencing entity may also have other function(s), such as to limit non-specific binding, to increase the hydrophilicity of the gel material, to enhance fluorescence properties, or combinations thereof. As such, the non-sequencing entity may be mono-functional, bi-functional, or multi-functional. Examples of the non-sequencing entity include a non-functional primer, a polymer strand, a peptide, and/or a fluorescence enhancer.

The "non-functional primer" is any single stranded nucleic acid sequence that will not participate in DNA or RNA synthesis. Examples of the non-functional primers include a poly T sequence or a poly A sequence. The length of the non-functional primer may be selected so that non-specific hybridization does not occur. As an example, the non-functional primer length may range from 3 to 10. In some instances, the non-functional primer length is less than 10 bases.

The "polymer strand" is a molecule composed of a few repeated monomer units (i.e., an oligomer) or many repeated monomer units (i.e., a polymer). The polymer strand may be linear, branched, or hyperbranched. Examples of branched polymers include star polymers, comb polymers, brush polymers, dendronized polymers, ladders, and dendrimers. In the examples disclosed herein, the polymer strand includes a terminal functional group at one end that can react with the gel material. In some instances, the other end of the polymer strand may include a terminal functional group that attaches a triplet state quencher, an anti-oxidant, or a dye. In these instances, the polymer strand may function as a linker, that links (attaches) the triplet state quencher, the anti-oxidant, or the dye to the gel material.

The "peptide" is a short chain of amino acid monomers linked by peptide (amide) bonds.

As used herein, the "sequencing primer" is defined as a single stranded nucleic acid sequence (e.g., single strand DNA or single strand RNA) that serves as a starting point for DNA or RNA synthesis. The 5' terminus of the sequencing primer may be modified to allow a coupling reaction with a gel material. The sequencing primer length can be any number of bases long and can include a variety of non-natural nucleotides. In an example, the sequencing primer is a short strand, including from 20 bases to 40 bases.

As used herein, a "site" refers to a location defined on or in a support where the gel material, the sequencing primer, and the non-sequencing entity may be attached.

The terms "substrate" and "support" are used interchangeably herein, and refer to a surface in which or on which the site is located. The support is generally rigid and is insoluble in aqueous liquid. The support may be inert to a chemistry that is used to modify the gel material. For example, a solid support can be inert to chemistry used to attach the sequencing primers and non-sequencing entity, to the gel material in a method set forth herein. Examples of suitable supports include glass and modified or functionalized glass, plastics (including acrylics, polystyrene and copolymers of styrene and other materials, polypropylene, polyethylene, polybutylene, polyurethanes, polytetrafluoroethylene (PTFE) (such as TEFLON® from Chemours), cyclic olefins/cyclo-olefin polymers (COP) (such as ZEONOR® from Zeon), polyimides, etc.), nylon, ceramics, silica or silica-based materials, silicon and modified silicon, carbon, metals, inorganic glasses, and optical fiber bundles.

As used herein, the terms "tetrazine" and "tetrazinyl" refer to six-membered heteroaryl group comprising four nitrogen atoms. Tetrazine can be optionally substituted.

"Tetrazole," as used herein, refer to five-membered heterocyclic group including four nitrogen atoms. Tetrazole can be optionally substituted.

The term "terminal functional group" refers to a functional group that is pendant on a non-sequencing entity and thus accessible for reaction with the gel material.

A "thiol" functional group refers to —SH.

As used herein, the term "well" refers to a discrete concave feature in a support having a surface opening that is completely surrounded by interstitial region(s) of the support surface. Wells can have any of a variety of shapes at their opening in a surface including, as examples, round, elliptical, square, polygonal, star shaped (with any number of vertices), etc. The cross-section of a well taken orthogonally with the surface can be curved, square, polygonal, hyperbolic, conical, angular, etc.

The aspects and examples set forth herein and recited in the claims can be understood in view of the above definitions.

Referring now to FIG. 1, an example of the array 10 is depicted. In general, the array 10 includes a substrate or support 12 and lines or flow channels 14 across the support 12. Each of the flow channels 14 includes multiple sites 16 which are separated from one another by interstitial regions 18. At each site 16, sequencing primer(s) 20 and a non-sequencing entity/entities 22 are deposited and attached to the gel material (24, 24', for example, in FIG. 2D).

The array 10 illustrated in FIG. 1 and discussed in the present disclosure may be disposed in or formed as a part of a flow cell, which is a chamber including a solid surface across which various carrier fluids, reagents, and so forth may be flowed. In an example, the flow cell may include the array 10 bonded to a top substrate through a sealing material (e.g., black polyimide or another suitable bonding material). The bonding takes place in bonding regions of the support 12, the sealing material, and the top substrate. The bonding regions may be located between the flow channels so that the sealing material physically separates one flow channel 14 from an adjacent flow channel 14 (to prevent cross-contamination) and may be located at the periphery of the flow cell (to seal the flow cell from external contamination). It is to be understood, however, that the bonding regions and the sealing material may be located in any desired region depending on the implementation. Bonding may be accomplished via laser bonding, diffusion bonding, anodic bonding, eutectic bonding, plasma activation bonding, glass frit bonding, or others methods known in the art.

Other examples of flow cells and related fluidic systems and detection platforms that can be integrated with the array 10 and/or readily used in the methods of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference in its entirety.

In some applications, the flow cell is used to perform controlled chemical or biochemical reactions in a reaction automation device, such as in a nucleotide sequencer. Ports 26 may be drilled through the support 12. By connecting to ports 26, the reaction automation device may control the flow of reagent(s) and product(s) in the sealed flow channels 14. The reaction automation device may, in some applications, adjust the pressure, temperature, gas composition and other environmental conditions of the flow cell. Further, in some applications, ports 26 may be drilled in the top substrate or in both the support 12 and the top substrate. In some applications, the reactions taking place in sealed flow channels 14 may be monitored through the top substrate and/or the support 12 by imaging or measurements of heat, light emission and/or fluorescence.

It is to be understood that the particular orientation of the flow channels 14, the sites 16, etc. may differ from those illustrated in FIG. 1. In some examples, the sites 16 are contiguous and thus need not be separated by interstitial regions 18.

The array 10 of FIG. 1, and examples of how the array 10 can be made, will now be described in more detail in reference to FIGS. 2A through 2D.

Figure 2A:
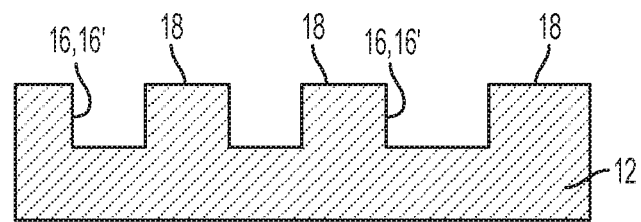
FIGS. 2A through 2D are cross-sectional views which together illustrate an example of the method disclosed herein.

FIG. 2A depicts the support 12 having sites 16 defined therein and separated by interstitial regions 18. This support 12 has a patterned surface. A "patterned surface" refers to an arrangement of different regions (i.e., sites 16) in or on an exposed layer of the solid support 12. For example, one or more of the sites 16 can be features where one or more sequencing (amplification) primers 20 and non-sequencing entities 22 are present. The features can be separated by the interstitial regions 18, where sequencing primers 20 and non-sequencing entities 22 are not present. Many different layouts of the sites 16 may be envisaged, including regular, repeating, and non-regular patterns. In an example, the sites 16 are disposed in a hexagonal grid for close packing and improved density. Other layouts may include, for example, rectilinear (i.e., rectangular) layouts, triangular layouts, and so forth. As examples, the layout or pattern can be an x-y format of sites 16 that are in rows and columns. In some other examples, the layout or pattern can be a repeating arrangement of sites 16 and/or interstitial regions 18. In still other examples, the layout or pattern can be a random arrangement of sites 16 and/or interstitial regions 18. The pattern may include spots, pads, wells, posts, stripes, swirls, lines, triangles, rectangles, circles, arcs, checks, plaids, diagonals, arrows, squares, and/or cross-hatches. Still other examples of patterned surfaces that can be used in the examples set forth herein are described in U.S. Pat. Nos. 8,778,849; 9,079,148; 8,778,848; and U.S. Patent Publication No. 2014/0243224, each of which is incorporated herein by reference in its entirety.

The layout or pattern may be characterized with respect to the density of the sites 16 (i.e., number of sites 16) in a defined area. For example, the sites 16 may be present at a density of approximately 2 million per mm². The density may be tuned to different densities including, for example, a density of at least about 100 per mm², about 1,000 per mm², about 0.1 million per mm², about 1 million per mm², about 2 million per mm², about 5 million per mm², about 10 million per mm², about 50 million per mm², or more. Alternatively or additionally, the density may be tuned to be no more than about 50 million per mm², about 10 million per mm², about 5 million per mm², about 2 million per mm², about 1 million per mm², about 0.1 million per mm², about 1,000 per mm², about 100 per mm², or less. It is to be further understood that the density of sites 16 on the support 12 can be between one of the lower values and one of the upper values selected from the ranges above. As examples, a high density array may be characterized as having sites 16 separated by less than about 15 µm, a medium density array may be characterized as having sites 16 separated by about 15 µm to about 30 µm, and a low density array may be characterized as having sites 16 separated by greater than about 30 µm.

The layout or pattern may also or alternatively be characterized in terms of the average pitch, i.e., the spacing from the center of the site 16 to the center of an adjacent interstitial region 18 (center-to-center spacing). The pattern can be regular such that the coefficient of variation around the average pitch is small, or the pattern can be non-regular in which case the coefficient of variation can be relatively large. In either case, the average pitch can be, for example, at least about 10 nm, about 0.1 µm, about 0.5 µm, about 1 µm, about 5 µm, about 10 µm, about 100 µm, or more. Alternatively or additionally, the average pitch can be, for example, at most about 100 µm, about 10 µm, about 5 µm, about 1 µm, about 0.5 µm about 0.1 µm, or less. The average pitch for a particular pattern of sites 16 can be between one of the lower values and one of the upper values selected from the ranges above. In an example, the sites 16 have a pitch (center-to-center spacing) of about 1.5 µm.

In some examples, the sites 16 are wells 16', and thus the support 12 includes an array of wells 16' in a surface thereof. The wells 16' (or other sites 16 with different configurations, such as shape, cross-section, etc.) may be fabricated using a variety of techniques, including, for example, photolithography, nanoimprint lithography, stamping techniques, embossing techniques, molding techniques, microetching techniques, printing techniques, etc. As will be appreciated by those in the art, the technique used will depend on the composition and shape of the support 12.

The wells 16' may be micro wells (having at least one dimension on the micron scale, e.g., about 1 m to about 1000 m) or nanowells (having at least one dimension on the nanoscale, e.g., about 1 nm to about 1000 nm). Each well 16' may be characterized by its volume, well opening area, depth, and/or diameter.

Each well 16' can have any volume that is capable of confining a liquid. The minimum or maximum volume can be selected, for example, to accommodate the throughput (e.g., multiplexity), resolution, analyte composition, or analyte reactivity expected for downstream uses of the array 10. For example, the volume can be at least about $1 \times 10^{-3}$ µm³, about $1 \times 10^{-2}$ m³, about 0.1 µm³, about 1 µm³, about 10 µm³, about 100 µm³, or more. Alternatively or additionally, the volume can be at most about $1 \times 10^4$ µm³, about $1 \times 10^3$ µm³, about 100 µm³, about 10 µm³, about 1 µm³, about 0.1 µm³, or less. It is to be understood that the gel material 24 can fill all or part of the volume of a well 16'. The volume of the gel material 24 in an individual well 16' can be greater than, less than or between the values specified above.

The area occupied by each well opening on a surface can be selected based upon similar criteria as those set forth above for well volume. For example, the area for each well opening on a surface can be at least about $1 \times 10^{-3}$ µm², about $1 \times 10^{-2}$ µm², about 0.1 µm², about 1 µm², about 10 µm², about 100 µm², or more. Alternatively or additionally, the area can be at most about $1 \times 10^3$ µm², about 100 µm², about 10 µm², about 1 µm², about 0.1 µm², about $1 \times 10^{-2}$ µm², or less.

The depth of each well 16' can be at least about 0.1 µm, about 1 µm, about 10 µm, about 100 µm, or more. Alternatively or additionally, the depth can be at most about $1 \times 10^3$ µm, about 100 µm, about 10 µm, about 1 µm, about 0.1 µm, or less.

In some instances, the diameter of each well 16' can be at least about 50 nm, about 0.1 µm, about 0.5 µm, about 1 µm, about 10 µm, about 100 µm, or more. Alternatively or additionally, the diameter can be at most about $1 \times 10^3$ µm, about 100 µm, about 10 µm, about 1 µm, about 0.5 µm, about 0.1 µm, about 50 nm, or less.

Figure 2B:
Figure 2B:
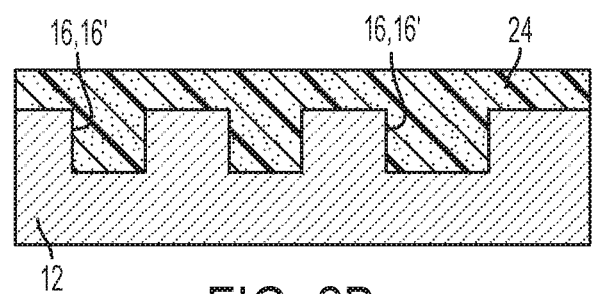
Figure 2C:
Figure 2C:
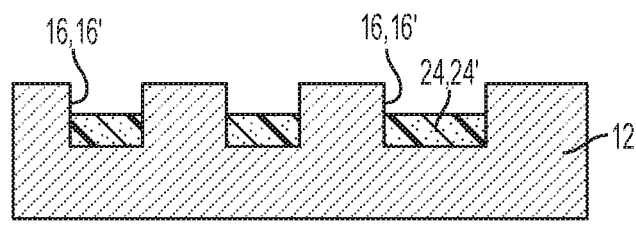

In the array 10 that is formed, the gel material 24 is positioned in each of the discrete wells 16'. Positioning the gel material 24 in each well 16' may be accomplished by first coating the patterned surface of the support 12 with the gel material 24, as shown in FIG. 2B, and then removing the gel material 24, for example via chemical or mechanical polishing, from at least the interstitial regions 18 on the surface of the structured support 12 between the wells 16'. In some examples, the gel material may be removed from the interstitial regions by washing steps that do not require chemical or mechanical polishing. These processes retain at least some of the gel material 24 in the wells 16' but remove or inactivate at least substantially all of the gel material 24 from the interstitial regions 18 on the surface of the structured support 12 between the wells 16'. As such, these processes create gel pads 24' (FIG. 2D) used for sequencing that can be stable over sequencing runs with a large number of cycles. In other examples, the gel material 24 is positioned in each well 16' by selective deposition techniques that likewise do not require chemical or mechanical polishing steps to remove the gel material from the interstitial regions.

Particularly useful gel materials 24 will conform to the shape of the site 16 where it resides. Some useful gel materials 24 can both (a) conform to the shape of the site 16 (e.g., well 16' or other concave feature) where it resides and (b) have a volume that does not at least substantially exceed the volume of the site 16 where it resides.

One example of a suitable gel material 24 includes a polymer with a recurring unit of Formula (I):

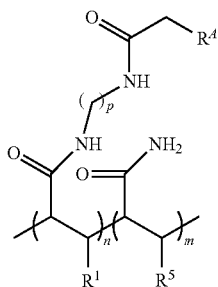

wherein:
$R^1$ is H or optionally substituted alkyl;
$R^4$ is selected from the group consisting of azido, optionally substituted amino, optionally substituted alkenyl, optionally substituted hydrazone, optionally substituted hydrazine, carboxyl, hydroxy, optionally substituted tetrazole, optionally substituted tetrazine, nitrile oxide, nitrone, and thiol; $R^5$ is selected from the group consisting of H and optionally substituted alkyl;
each of the —$(CH_2)_p$— can be optionally substituted;
p is an integer in the range of 1 to 50;
n is an integer in the range of 1 to 50,000; and
m is an integer in the range of 1 to 100,000.

Suitable polymers as Formula (I) are described, for example, in U.S. Patent Publication Nos. 2014/0079923 A1, or 2015/0005447 A1, each of which is incorporated herein by reference in its entirety). In the structure of Formula (I), one of ordinary skill in the art will understand that the "n" and "m" subunits are recurring subunits that are present in a random order throughout the polymer.

Specific examples of a polymer coating such as Formula (I) is poly(N-(5-azidoacetamidylpentyl)acrylamide-co-acrylamide (PAZAM), described, for example, in U.S. Patent Publication Nos. 2014/0079923 A1, or 2015/0005447 A1, which comprises the structure shown below:

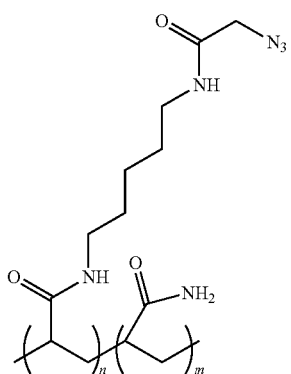

wherein n is an integer in the range of 1-20,000, and m is an integer in the range of 1-100,000. As with Formula (I), one of ordinary skill in the art will recognize that the "n" and "m" subunits are recurring units that are present in random order throughout the polymer structure.

The molecular weight of the Formula (I) polymer or PAZAM polymer may range from about 10 kDa to about 1500 kD, or may be, in a specific example, about 312 kDa.

In some examples, the Formula (I) polymer or PAZAM polymer is a linear polymer. In some other embodiments, the Formula (I) or PAZAM polymer is a lightly cross-linked polymer. In other examples, the Formula (I) or PAZAM polymer comprises branching. Other suitable polymers are co-polymers of SFA and SFA derivatized with a bromo-acetamide group (e.g., BRAPA), or co-polymers of SFA and SFA derivatized with an azido-acetamide group.

Other examples of suitable gel materials 24 include those having a colloidal structure, such as agarose; or a polymer mesh structure, such as gelatin; or a cross-linked polymer structure, such as polyacrylamide polymers and copolymers, silane free acrylamide (SFA, see, for example, U.S. Patent Publication No. 2011/0059865, which is incorporated herein by reference in its entirety), or an azidolyzed version of SFA. Examples of suitable polyacrylamide polymers may be formed from acrylamide and an acrylic acid or an acrylic acid containing a vinyl group as described, for example, in WO 2000/031148 (incorporated herein by reference in its entirety) or from monomers that form [2+2] photo-cycloaddition reactions, for example, as described in WO 2001/001143 or WO 2003/0014392 (each of which is incorporated herein by reference in its entirety).

The gel material 24 may be a preformed gel material. Preformed gel materials may be coated using spin coating, or dipping, or flow of the gel under positive or negative pressure, or techniques set forth in U.S. Pat. No. 9,012,022, which is incorporated herein by reference in its entirety. Dipping or dip coating may be a selective deposition technique, depending upon the support 12 and the gel material 24 that are used. As an example, the patterned support 12 is dipped into a preformed gel material 24, and the gel material 24 may fill the sites 16 selectively (i.e., the gel material 24 does not deposit on the interstitial regions 18), and polishing (or another removal process) may not be necessary.

Preformed polymer or PAZAM may be coated on the patterned support 12 using spin coating, or dipping, or flow of the gel under positive or negative pressure, or techniques set forth in U.S. Pat. No. 9,012,022. The attachment of the polymer or PAZAM may also take place via a surface initiated atom transfer radical polymerization (SI-ATRP) to a silanized surface. In this example, the support 12 surface may be pre-treated with APTS (methoxy or ethyoxy silane) to covalently link silicon to one or more oxygen atoms on the surface (without intending to be held by mechanism, each silicon may bond to one, two or three oxygen atoms). This chemically treated surface is baked to form an amine group monolayer. The amine groups are then reacted with Sulfo-HSAB to form an azido derivative. UV activation at 21° C. with 1 J/cm$^2$ to 30 J/cm$^2$ of energy generates an active nitrene species, which can readily undergo a variety of insertion reactions with the PAZAM.

Other examples for coating PAZAM on the support 12 are described in U.S. Patent Publication No. 2014/0200158, which is incorporated herein by reference in its entirety), and include ultraviolet (UV) mediated linking of PAZAM monomers to an amine-functionalized surface, or a thermal linkage reaction involving an active group (acryloyl chloride or other alkene or alkyne-containing molecule) with subsequent deposition of PAZAM and application of heat. In some examples, the surface 30 is modified with alkenyl or cycloalkenyl groups, which can then react with azido-functionalized polymers such as PAZAM or those comprising azido-derivatized SFA, under conditions such as click chemistry, to form covalent bonds between the modified surface and the polymer.

In still other examples, the PAZAM may be deposited on the support 12, which includes, at its surface, a silane or silane derivative that can attach to a functional group of the PAZAM. For example, the silane or silane derivative may contain an unsaturated moiety (e.g., cycloalkenes, cycloalkynes, heterocycloalkenes, heterocycloalkynes, substituted variants thereof, and combinations thereof) that can covalently attach to a functional group of the PAZAM. Examples of cycloalkene unsaturated moieties include norbornene, a norbornene derivative (e.g., a (hetero)norbornene including an oxygen or nitrogen in place of one of the carbon atoms), transcyclooctene, transcyclooctene derivatives, transcyclopentene, transcycloheptene, trans-cyclononene, bicyclo[3.3.1]non-1-ene, bicyclo[4.3.1]dec-1 (9)-ene, bicyclo[4.2.1]non-1(8)-ene, and bicyclo[4.2.1]non-1-ene. Any of these cycloalkenes can be substituted as described in U.S. Patent Publication No. 2015/0005447, which is incorporated herein by reference in its entirety. An example of the norbornene derivative includes [(5-bicyclo[2.2.1]hept-2-enyl)ethyl]trimethoxysilane. Examples of cycloalkyne unsaturated moieties include cyclooctyne, a cyclooctyne derivative, or bicyclononynes (e.g., bicyclo[6.1.0]non-4-yne or derivatives thereof, bicyclo[6.1.0]non-2-yne, or bicyclo [6.1.0]non-3-yne). These cycloalkynes can also be substituted as described in U.S. Patent Publication No. 2015/0005447.

In these examples, the PAZAM may be deposited on the surface of the silanized support 12 using spin coating, or dipping or dip coating, or flow of the functionalized molecule under positive or negative pressure, or techniques set forth in U.S. Pat. No. 9,012,022. For deposition, the PAZAM may be present in a solution (e.g., an ethanol and water mixture). After being deposited, the PAZAM solution may also be exposed to a curing process to form the gel material 24.

The gel material 24 may be a liquid that subsequently forms the gel material 24. An example of applying liquid that subsequently forms the gel material 24 is the coating of an array of sites 16 with silane free acrylamide and N-[5-(2-bromoacetyl) aminopentyl]acrylamide (BRAPA) in liquid form and allowing the reagents to form a gel by polymerization on the surface. Another example involves coating of an array of sites 16 with PAZAM monomers in liquid form and allowing the reagents to form a gel by polymerization on the surface. Coating of an array in this way can use chemical reagents and procedures as set forth in U.S. Patent Publication No. 2011/0059865.

The gel material 24 may be covalently linked to the support 12 (at the sites 16) or may not be covalently linked to the support 12. The covalent linking of the gel material 12 to the sites 16 is helpful for maintaining the gel in the structured sites 16 throughout the lifetime of the array 10 during a variety of uses. The following are some examples of reactions that can take place between PAZAM and a silane or silane derivative on some examples of the support 12, which lead to covalent linkages.

When the silane or silane derivative on the support 12 includes norbornene or a norbornene derivative as the unsaturated moiety, the norbornene or a norbornene derivative can: i) undergo a 1,3-dipolar cycloaddition reaction with an azide/azido group of PAZAM; ii) undergo a coupling reaction with a tetrazine group attached to PAZAM; undergo a cycloaddition reaction with a hydrazone group attached to PAZAM; undergo a photo-click reaction with a tetrazole group attached to PAZAM; or undergo a cycloaddition with a nitrile oxide group attached to PAZAM.

When the silane or silane derivative on the support 12 includes cyclooctyne or a cyclooctyne derivative as the unsaturated moiety, the cyclooctyne or cyclooctyne derivative can: i) undergo a strain-promoted azide-alkyne 1,3-cycloaddition (SPAAC) reaction with an azide/azido of PAZAM, or ii) undergo a strain-promoted alkyne-nitrile oxide cycloaddition reaction with a nitrile oxide group attached to PAZAM.

When the silane or silane derivative on the support 12 includes a bicyclononyne as the unsaturated moiety, the bicyclononyne can undergo similar SPAAC alkyne cycloaddition with azides or nitrile oxides attached to PAZAM due to the strain in the bicyclic ring system.

While several examples of covalent linkages between the support 12 and the gel material 24 are provided, as noted above and in many examples, the gel material 24 need not be covalently linked to the sites 16. For example, silane free acrylamide, SFA, is not covalently attached to any part of the support 12.

As mentioned above, FIG. 2C illustrates the removal of the gel material 24 from the interstitial regions 18. Removal may be accomplished via polishing. Polishing may be a mechanical and/or chemical treatment process.

Mechanical polishing can be carried out by applying abrasive forces to the surface of the solid support 12 (having the gel material 24 thereon). Example methods include abrasion with a slurry of beads, wiping with a sheet or cloth, scraping, or the like. It will be understood that beads used for polishing may or may not be spherical, and can have irregular shapes, polygonal shapes, ovoid shapes, elongated shapes, cylindrical shapes, etc. The surface of the beads can be smooth or rough. Any of a variety of particles can be useful as beads for polishing. One example of polishing includes using a lintless (cleanroom grade) wipe coated with a 3 µm silica bead slurry (10% w/v in water) to remove the gel material 24 from the interstitial regions 18. A polishing wheel/grinder can also be used with this or another slurry.

Still another example of mechanical polishing can also be achieved using a fluid jet or gas (e.g., air or inert gas such as argon or nitrogen) jet to remove gel from interstitial regions 18.

Chemical polishing techniques, such as hydrolysis or radical-based degradation of acrylamide (e.g., via exposure to benzoyl peroxide or dilute hydrogen peroxide) may also be used. During this form of polishing, the chemicals can be provided in a solid, liquid, gas or plasma state. Accordingly, plasma polishing can be useful in some examples.

Polishing can also involve a combination of chemical and mechanical polishing methods where a chemical slurry containing a colloidal suspension of particles is used to mechanically exfoliate and then chemically dissolve displaced portions of gel material 24 from interstitial regions 18. In an example, a chemical mechanical polishing system, e.g., a wafer polisher including a Strasbaugh ViPRR II, or other suitable polishing head, may be used to remove the gel material 24 from the interstitial regions 18 without deleteriously affecting the underlying support 12 at those regions 18. This type of polishing system may be used with the previously described silica bead slurry, or with a gentler chemical slurry. In an example, the gentle chemical slurry is a basic, aqueous slurry including an abrasive particle selected from the group consisting of calcium carbonate ($CaCO_3$) and poly(methyl methacrylate) (PMMA). The average particle size of the $CaCO_3$ may range from about 15 nm to about 5 µm, and in one example is about 700 nm. In addition to the $CaCO_3$, the basic, aqueous slurry may also include a buffer, a chelating agent, a surfactant, and/or a dispersant. An example of the buffer includes tris base (i.e., tris(hydroxymethyl)aminomethane), which may be present in a solution having a pH of about 9. An example of the chelating agent is ethylenediaminetetraacetic acid (EDTA), which may be present in a solution having a pH of about 8. An example of the surfactant is sodium dodecyl sulfate. Polyacrylate dispersants having different molecular weights may be used. An example of the dispersant is poly(acrylic acid sodium salt).

Other methods to polish or clean the interstitial regions 18 include adhesive based techniques, for example, techniques wherein a rigid, planar adhesive film with affinity to the gel material 24 is applied, thereby making intimate contact (e.g., via chemical linkage) with the gel material 24 in interstitial regions 18. The mechanical removal/peeling of this adhesive film will result in the mechanical removal of the gel material 24 from interstitial regions 18, while leaving gel material 24 in the sites 16.

In one example, thiophosphate-grafted SFA can be removed from interstitial regions 18 on a support 12 surface as follows: a water-dampened Whatman wipe can be dabbed into aluminum oxide (~100 mg, 0.3 um) or steel beads, and then the formed slurry can be rubbed on the surface of the support (having the thiophosphate-grafted SFA thereon), in small concentric circles, using even pressure, and then a clean water-wet Whatman wipe can be used to remove the slurry and the thiophosphate-grafted SFA from the surface.

The mechanical and chemical polishing methods exemplified herein for removing gel material 24 from interstitial regions 18 can also be used to inactivate gel material at interstitial regions 18, whether or not the gel material 24 is removed. For example, the gel material 24 can be inactivated with respect to the ability to attach the sequencing primer 20 and the non-sequencing entity 22.

After the gel material 24 is positioned in each well 16', the sequencing primer(s) 20 and the non-sequencing entity/entities 22 are grafted to the gel material 24. In some examples, the primer(s) 20 may be grafted before or after the non-sequencing entity/entities 22 is/are grafted to the gel material 24. In other examples, the primer(s) 20 and the non-sequencing entity/entities 22 are co-grafted to the gel material 24.

Sequential grafting may be accomplished by exposing the support 12 (having the gel material 24 in the sites 16) to a solution or mixture containing the sequencing primer(s) 20 and incubating, and then to a solution or mixture containing the non-sequencing entity 22 and incubating. Alternatively, sequential grafting may be accomplished by exposing the support 12 (having the gel material 24 in the sites 16) to a solution or mixture containing the non-sequencing entity 22 and incubating, and then to a solution or mixture containing the sequencing primer(s) 20 and incubating.

Co-grafting may be accomplished by exposing the support 12 (having the gel material 24 in the sites 16) to a solution or mixture containing the sequencing primer(s) 20 and the non-sequencing entity 22, and then incubating. Exposure of the support 12 to this solution or mixture may be accomplished by depositing a mixture of the sequencing primer(s) 20 and the non-sequencing entity 22 onto the support 12. In an example, the solution or mixture may be drawn across the gel material 24 coated support 12 (shown in FIG. 2C).

In any of the grafting examples, incubation takes place at a predetermined temperature which depends, in part, upon the sequencing primer(s) 20 and the non-sequencing entity 22 used. As examples, incubation may be accomplished at a temperature ranging from room temperature (i.e., about 25° C.) to about 60° C.

Also in any of the grafting examples, the solution may include the sequencing primer(s) 20 and/or the non-sequencing entity 22, water, a buffer, and a catalyst. The molar ratio of non-sequencing entity 22 to sequencing primer 20, whether present in the same solution/mixture or separate solutions/mixtures, ranges from about 0.25:1 to about 5:1.

Examples of suitable sequencing primers 20 include forward amplification primers or reverse amplification primers. Examples of suitable sequencing primers 20 include P5 or P7 primers. The P5 and P7 primers are used on the surface of commercial flow cells sold by Illumina Inc. for sequencing on HiSeq®, HiSeqX®, MiSeq®, NextSeq® and Genome Analyzer® instrument platforms. The P5 and P7 primer sequences include the following:

(SEQ. ID NO. 1)
P5: 5'-AATGATACGGCGACCACCGAGA(dU)CTACAC (SEQ. ID NO. 2)
P7: 5'-CAAGCAGAAGACGGCATACGAG*AT wherein G* is an 8-oxoguanine.

Optionally, one or both of the P5 and P7 primers can include a poly T tail. The poly T tail is generally located at the 5' end of the sequence, but in some cases can be located at the 3' end. The poly T sequence can include any number of T nucleotides, for example, from 2 to 20.

The P5 and P7 primers, as well as other sequencing primers 20, may be modified at the 5' end with a group that is capable of reacting with a functional group of the gel material 24. One example of a suitable functional group is bicyclo[6.1.0] non-4-yne (BCN), which can react with an azide of the gel material 24. Other example terminated primers include a tetrazine terminated primer, a norbornene terminated primer, an alkyne terminated primer, an amino terminated primer, an epoxy or glycidyl terminated primer, a thiophosphate terminated primer, and a triazolinedione terminated primer. In some embodiments, terminated primers include an alkyne terminated primer. In other embodiments, terminated primers include a thiophosphate terminated primer. One of skill in the art will understand how to design and use sequencing primers 20 that are suitable for capture and amplification of nucleic acids as presented herein.

Examples of suitable non-sequencing entities 22 include the non-functional primer, the polymer strand, the peptide, and/or the fluorescence enhancer.

As mentioned above, the non-functional primer is any single stranded nucleic acid sequence that, in its as-grafted form, will not participate in DNA or RNA synthesis. Examples include a poly T sequence or a poly A sequence.

Examples of the polymer strand include a dendrimer (e.g., poly(amido amine or PAMAM), polydextran, methacryloyloxyethyl phosphorylcholine (PCA), poly(ethylene glycol) (PEG, i.e., poly(ethylene oxide) or PEO), poly(ethylene imine) (PEI), poly-L-lysine (PLL), propargyl methacrylate (PMA), poly(methyl methacrylate) (PMMA), poly(N-isopropylacrylamide) (PNIPAM), poly(ethylene glycol) acrylate (POEGA), poly(propylene imine) (PPI, which is a dendrimer core), poly(vinyl alcohol) (PVA), poly(2-ethyl-2-oxazoline), polyacrylic acid (PAA), and poly(trolox ester).

Each of these polymer strand materials may function as spacers to create additional space between the sequencing primers 20 that are attached to the gel material 24. Some of these polymer strand materials also have properties that can add hydrophilicity to the gel material 24 and limit non-specific binding on the gel material 24. An example of this polymer strand material includes PEG. In the examples disclosed herein, PEG has a molecular weight ranging from about 0.5 KDa to about 10 KDa. Other polymer strand materials are also multi-functional, for example, poly(trolox ester) may be a spacer and may be an anti-oxidant.

The polymer strand either includes a functional group that can react with group(s) of the gel material 24, or is modified to include a functional group that can react with group(s) of the gel material 24. Examples of such functional groups include an alkyne, a norbornyl, a copper free click moiety (e.g., dibenzocyclooctyne (DIBO) or others), and a thiol. Alkynes, norbornyls, and copper free click moieties may react with azides of PAZAM via click reactions. Thiols may react with SFA. An example of a polymer strand material that includes one of the listed functional groups is PMA, which includes an alkyne. Examples of modified polymer strands include alkyne terminated PEG, alkyne terminated PMMA, norbornyl terminated PMMA, thiol terminated PNIPAM, alkyne terminated PVA, thiol terminated PVA, alkyne terminated PAA, and thiol terminated PAA.

In some examples, the polymer strands as described may be grafted to the gel material 24 as the non-sequencing entity 22.

In other examples, the polymer strands as described may be a linker molecule that attaches a fluorescence enhancer, such as a triplet state quencher, an anti-oxidant, or a FRET donor, to the gel material 24. For example, the polymer strand may be terminated with an alkyne on one end to attach to the gel material 24, and a functional group (e.g., thiol, amine, aldehyde, or carboxylic acid) on the other end to attach to the triplet state quencher, the anti-oxidant, or the FRET donor.

Examples of suitable triplet state quenchers are selected from the group consisting of cyclo-octyltetraene (COT), Trolox (6-hydroxy-2,5,7,8-tetramethylchroman-2-carboxylic acid (Hoffmann-La Roche AG)), and nitrobenzyl alcohol (NBA). Examples of suitable anti-oxidants are selected from the group consisting of ascorbate, glutathione, gallic acid, catechin, Trolox, and vitamin E. The attached FRET donor is tailored or selected to have an optimal spectral overlap and FRET efficiency with the fully functional nucleotides (FFN) (dye detected in sequencing, incorporated in sequencing-by-synthesis (SBS)). Examples of the FRET donor are selected from the group consisting of a donor dye to FRET with a green-emitting dye (incorporated in nucleotides in a sequencing workflow) and a donor dye to FRET with a red-emitting dye (incorporated in nucleotides in a sequencing workflow). Specific examples of donor dyes to FRET with green-emitting fully functional nucleotides (FFNs) include Cy2® (cyanine dye, Jackson ImmunoResearch Laboratories, Inc.), Alexa Fluor® dyes (e.g., 488) (ThermoFisher Scientific), and Atto dyes (e.g., 465, 488, and 490) (Atto-Tec); and specific examples of donor dyes to FRET with red-emitting FFNs include Cy3® (cyanine dye, Jackson ImmunoResearch Laboratories, Inc.), Alexa Fluor® dyes (e.g., 546, 555, 568, and 594) (ThermoFisher Scientific), and Atto dyes (e.g., 532) (Atto-Tec). The FRET donors may be suitable for use in one or two dye sequencing by synthesis configurations involving 542 nm, 550 nm, 565 nm (wavelength of absorption) and/or Rhodamine 6G.

In these other examples, the polymer strands and the attached fluorescence enhancer together make up the non-sequencing entity 22. In these other examples, the other end of the polymer strand (e.g., the end opposed to the end that is attached to gel material 24) either includes a functional group that can incorporate or react with group(s) of the fluorescence enhancer, or is modified to include a functional group that can incorporate or react with group(s) of the fluorescence enhancer. Examples of such functional groups include a thiol, an amine, an aldehyde, and a carboxylic acid. Other functional groups that can attach the fluorescence enhancer to the polymer strand may be used as well.

As examples, vitamin E may be conjugated to PAA, and glutathione, ascorbic acid, gallic acid or catechin may be conjugated to PEG or PMMA.

As other examples, the FRET donor may be conjugated to any of the polymer strands having or modified with an alkyne group.

Still another example of the non-sequencing entity is a peptide.

Figure 2D:
Figure 2D:
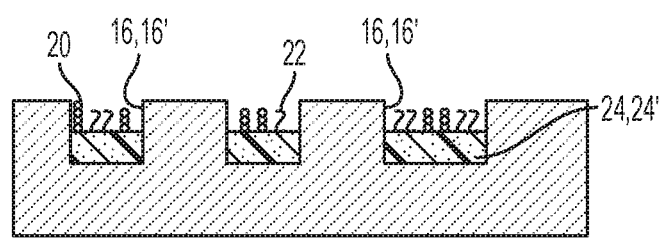
Figure 3:
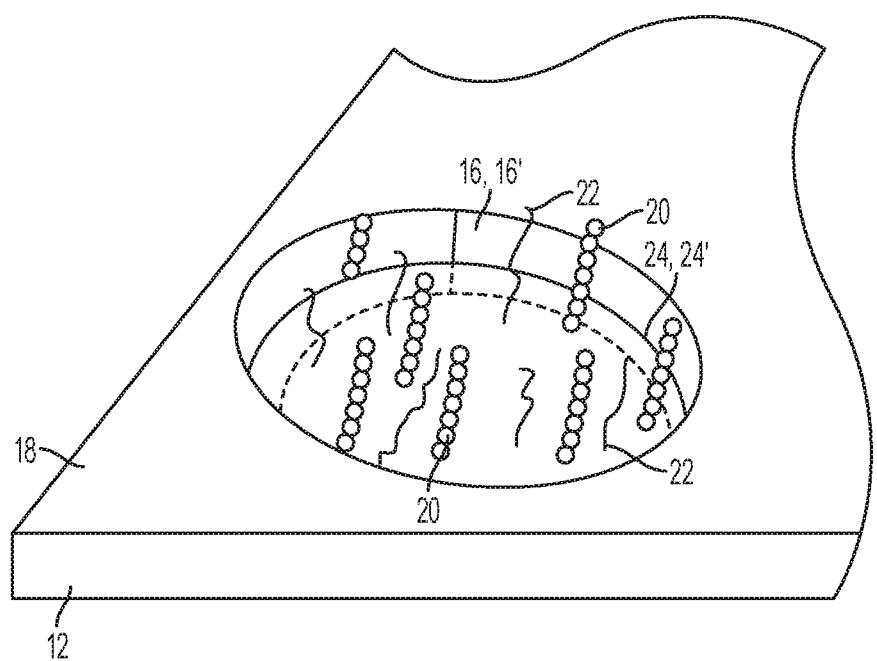
FIG. 3 is an enlarged, perspective cut-away view of one of the individual sites shown in FIGS. 1 and 2D.

The as-grafted sequencing primer(s) 20 and non-sequencing entity/entities 22 are shown in FIGS. 2D and 3. The molar ratio of grafted non-sequencing entity 22 to grafted sequencing primer 20 ranges from about 0.25:1 to about 5:1. In another example, the molar ratio of grafted non-sequencing entity 22 to grafted sequencing primer 20 ranges from about 0.5:1 to about 2:1. The as-grafted non-sequencing entity/entities 22 will not participate in subsequently performed sequencing techniques, but rather space apart the sequencing primer(s) 20 in the site 16 and may provide additional functionality to the site 16.

The array 10 disclosed herein may be used in a variety of sequencing approaches or technologies, including techniques often referred to as sequencing-by-synthesis (SBS), sequencing-by-ligation, pyrosequencing, and so forth. With any of these techniques, since the gel material 24 and attached sequencing primers 20 are present in the sites 16 and not on the interstitial regions 18, amplification will be confined to the various sites 16.

Briefly, a sequencing by synthesis (SBS) reaction may be run on a system such as the HiSeq®, HiSeqX®, MiSeq® or NextSeq® sequencer systems from Illumina (San Diego, Calif.). A set of target DNA molecules to be sequenced is hybridized to the bound sequencing primers 20 (and not to the non-sequencing entity 22) and then amplified by bridge amplification or by kinetic exclusion amplification. Denaturation leaves single-stranded templates anchored to the gel material 24, and several million dense clusters of double-stranded DNA are generated (i.e., cluster generation). The sequencing reactions are carried out, and in some examples, the sequencing primers 20 and non-sequencing entities 22 (and amplicons including primers extended during amplification steps to include copies of the target DNA) are then unbound from the gel material 24 so that the surface is reusable in future sequencing reactions. Thus, one or more of the steps of attaching sequencing primers 20 and non-sequencing entities 22 to the gel material 24, hybridizing target DNA molecules to the sequencing primers 20, bridge amplification, sequencing the target DNA, and removing sequencing primers 20 and non-sequencing entities 22 and amplicons can be repeated. One or more repetitions can be carried out.

To further illustrate the present disclosure, examples are given herein. It is to be understood that these examples are provided for illustrative purposes and are not to be construed as limiting the scope of the present disclosure.

EXAMPLES

Example 1

Sequencing primers (e.g., P5/P7 with poly T tails) were grafted with a non-sequencing primer (i.e., 5'-hexyne-TTT, referred to as NSP) in wells of a flow cell available from Illumina, Inc. The molar ratio of the non-sequencing primer to the sequencing primer was varied among the samples. The sequencing primer was used without a non-sequencing primer for two control samples.

A mixture was prepared for each sample. The mixture included ultrapure water, a buffer, and an excess of catalysts (e.g., $CuSO_4$ (20 mM-200 mM), ascorbate (20 mM-200 mM), and pentamethyldiethylenetriamine (PMDTA) (105 mM-1050 mM). The concentration of the sequencing primer(s) was about 1 µM. The total amount of catalyst was the same in each sample. The molar ratio of the non-sequencing primer (NSP) to the sequencing primer (P5/P7) is shown in Table 1.

TABLE 1

| | Flow CellLane | | | | | | |
|---|---|---|---|---|---|---|---|
| | 1 | 2 | 3 | 4 | 5 | 6 | 7 |
| Sample | Control 1 | 2 | 3 | 4 | Control 5 | 6 | 7 |
| NSP:P5/P7 | 0:1 | 2:1 | 5:1 | 10:1 | 0:1 | 20:1 | 50:1 |

Each mixture was applied to a respective flow cell lane and incubated at about 60° C. The flow cell was washed to remove unbound primers.

Figure 4:
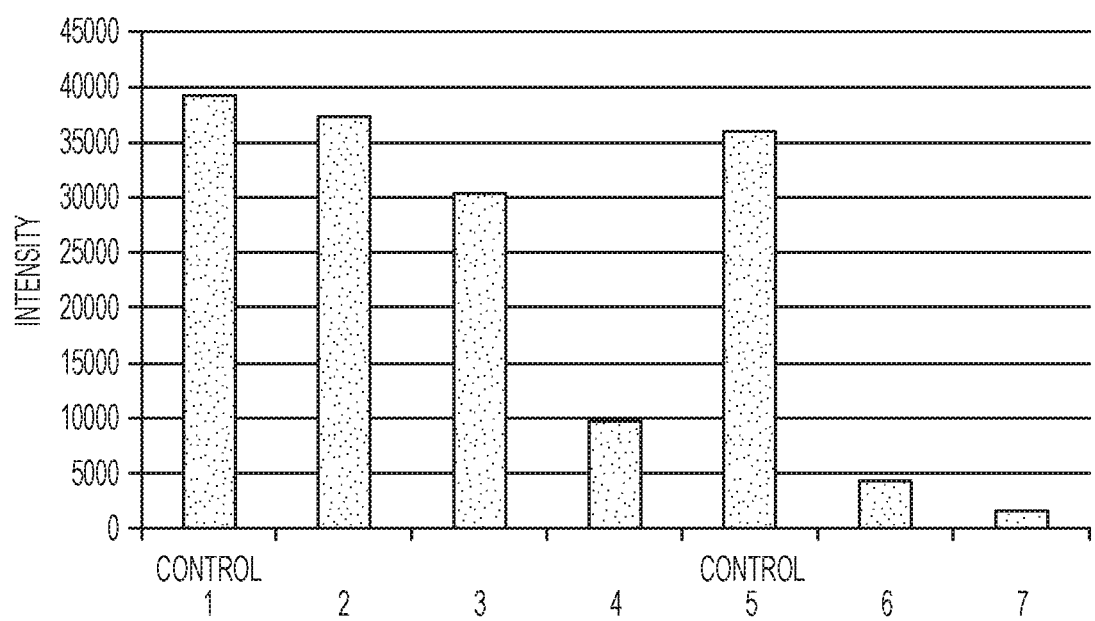
FIG. 4 is a graph depicting, in one example, tetrachloro fluorescein (TET) quality control (QC) results, in terms of intensity, for lanes including different molar ratios of a non-sequencing primer to a sequencing primer.

A tetrachloro-fluorescein (TET) mixture including a buffer and TET oligos (i.e., dye labeled oligonucleotides having complementary sequences to the T10 primers) was applied to the flow cell lanes to stain the surface sequencing primers. TET can be hybridized to the P10 primers on a surface; the excess TET can be washed away, and the attached dye concentration (in terms of intensity) can be measured by fluorescence detection using a scanning instrument, such as a Typhoon Scanner (General Electric). From the intensity data, spatial distribution and primer density can be determined. The results are shown in FIG. 4. The results indicate that grafting of the sequencing primers with the non-sequencing primer was comparable to grafting of the sequencing primers without the non-sequencing primer at molar ratios below 10:1.

Example 2

Sequencing primers (e.g., P5/P7 with poly T tails) were grafted with a non-sequencing primer (i.e., 5'-hexyne-TTT) in wells of a flow cell available from Illumina, Inc. The molar ratio of the non-sequencing primer to the sequencing primer was varied among the samples. The sequencing primer was used without a non-sequencing primer for one control sample.

A mixture was prepared for each sample. The mixture included ultrapure water, a buffer, and an excess of catalysts (e.g., $CuSO_4$ (20 mM-200 mM), ascorbate (20 mM-200 mM), and pentamethyldiethylenetriamine (PMDTA) (105 mM-1050 mM). The concentration of the P5/P7 sequencing primers was about 1 µM. The total amount of catalyst varied for some of the mixtures. The molar ratio of the non-sequencing primer to the sequencing primer and the variations in catalyst amount are shown in Table 2.

TABLE 2

| | Flow Cell Lane | | | | | | |
|---|---|---|---|---|---|---|---|
| | 1 | 2 | 3 | 4 | 5 | 6 | 7 |
| Sample | 8 | 9 | Control 10 | 11 | 12 | 13 | 14 |
| NSP:P5/P7 | 0.25:1 | 0.5:1 | 0:1 | 1:1 | 2:1 | 2:1 | 5:1 |
| Total Catalyst | 1X* | 1X | 1X | 1X | 1.5X | 1X | 4X |

*X = a base amount of all three catalysts

Each mixture was applied to a respective flow cell lane and incubated at about 60° C. The flow cell was washed to remove unbound primers.

Figure 5:
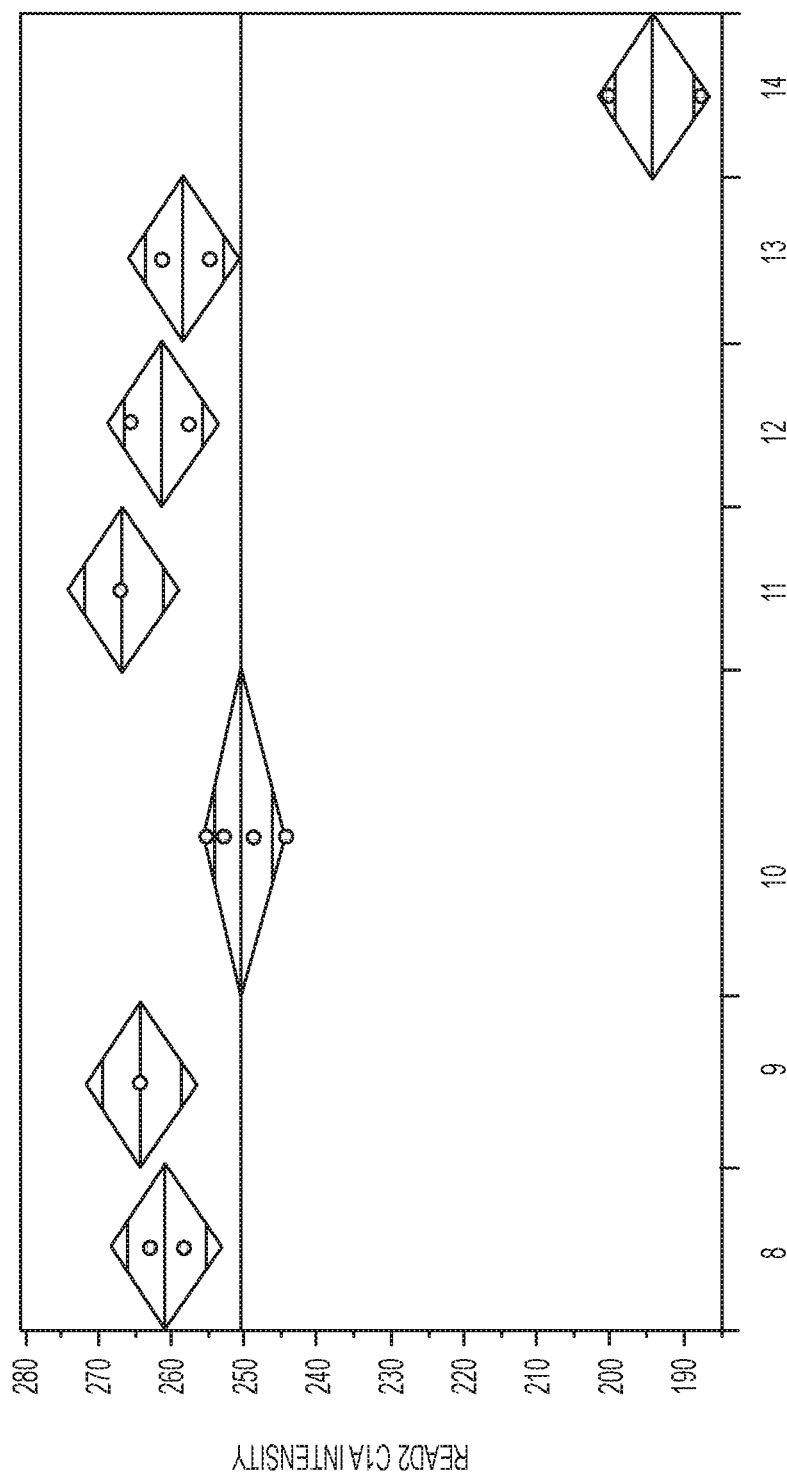
FIG. 5 is a graph depicting, in one example, the Read2 C1A Intensity for different molar ratios of a non-sequencing primer to a sequencing primer.

The flow cell was exposed to hybridization for imaging, clustering, and sequencing. Read 2 C1A intensities were measured, and these results are shown in FIG. 5. These results illustrate that grafting of the sequencing primer with the non-sequencing primer without an excess of catalyst can increase sequencing intensity.

Example 3

P5/P7 sequencing primers with poly T tails were grafted with a polymer strand, as the non-sequencing entity (referred to as non-sequencing polymer strand or NSPS), to two flow cells available from Illumina Inc. The polymer strand was PEG-alkyne, and the molecular weight of the PEG alkyne was varied among the samples. The molar ratio of the non-sequencing polymer strand to the sequencing primer was also varied among the samples. The sequencing primer was used without the non-sequencing polymer strand for four control samples.

Two mixtures were prepared. A sequencing primer mixture included ultrapure water, a buffer, and an excess of catalysts (e.g., $CuSO_4$ (20 mM-200 mM), ascorbate (20 mM-200 mM), and pentamethyldiethylenetriamine (PMDTA) (105 mM-1050 mM). The concentration of the P5/P7 sequencing primers was about 1 M. Freshly prepared PEG-alkyne solutions were used (e.g., different molecular weight PEG-alkynes were dissolved in water).

The sequencing primer mixture was applied to a respective flow cell lane, with or without one of the non-sequencing polymer strand solutions at desired molar ratios, as shown in Table 3. Table 3 also indicates the PEG-alkyne molecular weight that was used in each lane. The flow cells were incubated at about 60° C., and washed to remove unbound materials.

TABLE 3

| FLOW CELL 1 | | | | | | | | |
|---|---|---|---|---|---|---|---|---|
| | Lane | | | | | | | |
| | 1 | 2 | 3 | 4 | 5 | 6 | 7 | 8 |
| Sample | Control 15 | 16 | 17 | 18 | 19 | Control 20 | 21 | 22 |
| NSPS:P5/P7 | 0:1 | 0.5:1 | 2:1 | 0.5:1 | 2:1 | 0:1 | 0.5:1 | 2:1 |
| PEG-alkyne MW (KDa) | N/A | 0.5 | 0.5 | 1 | 1 | N/A | 2 | 2 |

| FLOW CELL 2 | | | | | | | | |
|---|---|---|---|---|---|---|---|---|
| | Lane | | | | | | | |
| | 1 | 2 | 3 | 4 | 5 | 6 | 7 | 8 |
| Sample | Control 23 | 24 | 25 | 26 | Control 27 | 28 | 29 | 30 |
| NSPS:P5/P7 | 0:1 | 0.5:1 | 1:1 | 2:1 | 0:1 | 0.5:1 | 1:1 | 2:1 |
| PEG-alkyne MW (KDa) | N/A | 5 | 5 | 5 | N/A | 10 | 10 | 10 |

Figure 6A:
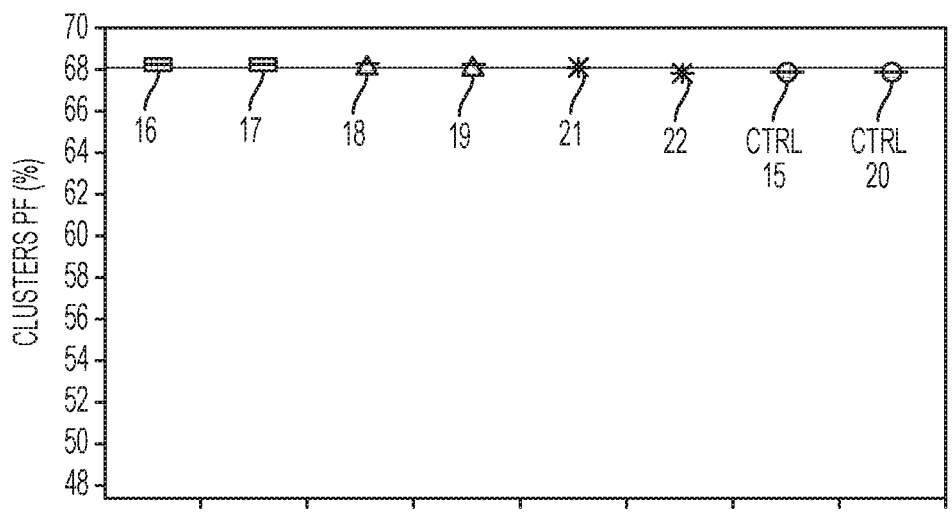
FIGS. 6A and 6B are graphs depicting, in one example, the percentage of clusters passing through a filter for different molar ratios of a polymer strand non-sequencing entity to a sequencing primer.
Figure 6B:
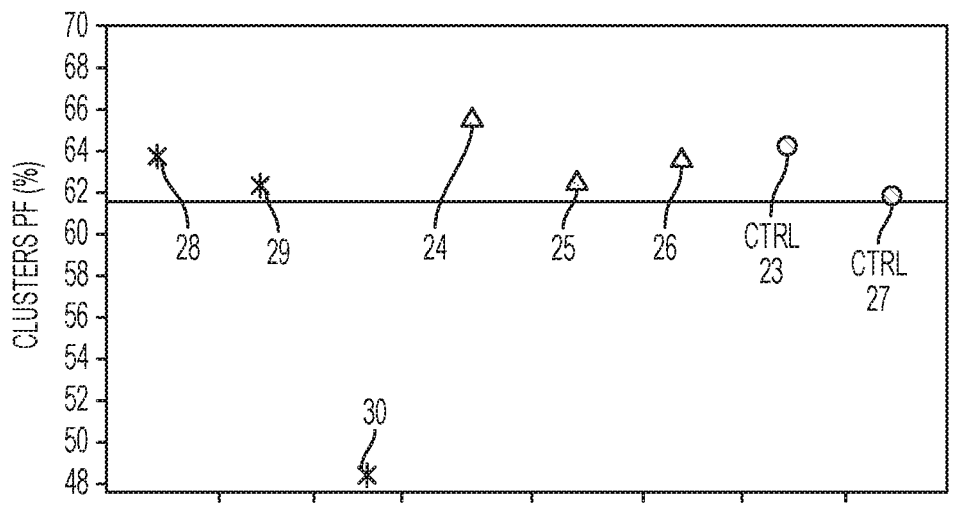
Figure 7A:
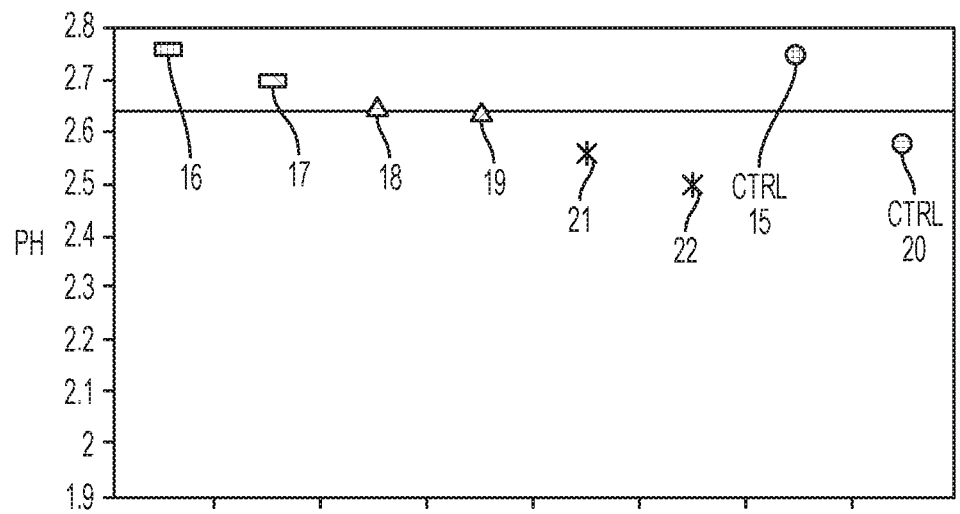
FIGS. 7A and 7B are graphs depicting, in one example, the percentage of pad hopping for different molar ratios of a polymer strand non-sequencing entity to a sequencing primer.
Figure 7B:
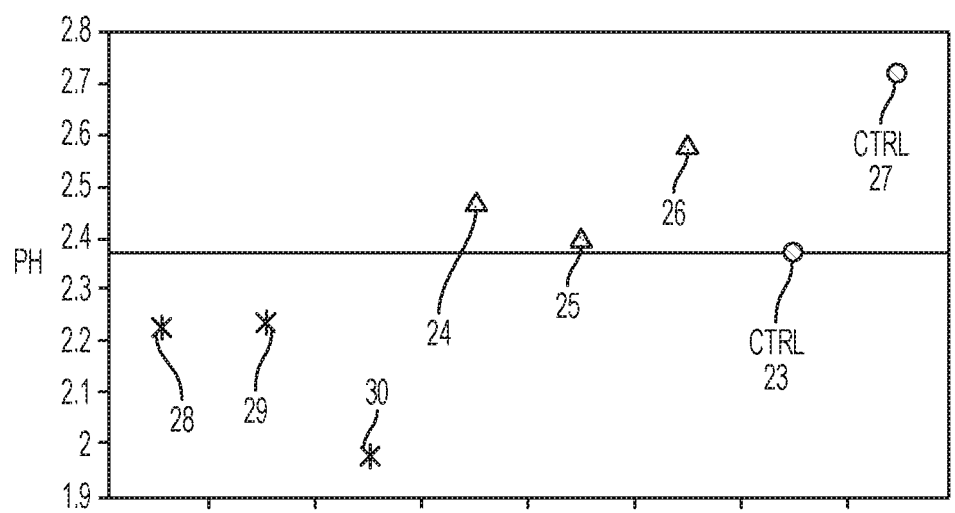

The flow cells were exposed to hybridization for imaging, clustering, and sequencing. The sequencing data was collected, and the results for the percentage of clusters passing through a filter (% passing filter (PF)) are shown in FIGS. 6A (flow cell 1) and 6B (flow cell 2) and the results for pad hopping (PH) are shown in FIGS. 7A (flow cell 1) and 7B (flow cell 2). % Passing filter (PF) is the metric used to describe clusters which pass a chastity threshold and are used for further processing and analysis of sequencing data. % Pad hopping is a metric describing the amount of duplicate clusters located within the vicinity of a unique cluster. Higher % passing filter and lower % pad hopping result in increased yield of unique clusters used for sequencing data. These results illustrate that grafting of the sequencing primers with the lower molecular weight PEG-alkyne (i.e., KDa>10) was comparable to grafting of the sequencing primers without any PEG-alkyne. As such, the introduction of the polymer strand non-sequencing entity does not deleteriously affect the sequencing results, and may add hydrophilicity to the gel material in the flow cell wells, limit non-specific binding, etc.

Additional Notes

It should be appreciated that all combinations of the foregoing concepts (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

All publications, patents, and patent applications cited in this Specification are hereby incorporated by reference in their entirety.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is to be understood that the ranges provided herein include the stated range and any value or sub-range within the stated range. For example, a range from about 0.5 KDa to less than about 10 KDa should be interpreted to include not only the explicitly recited limits of from about 0.5 KDa to less than about 10 KDa, but also to include individual values, such as about 0.8 KDa, about 3.25 KDa, about 5 KDa, about 7.5 KDa, etc., and sub-ranges, such as from about 4.25 KDa to about 9 KDa, from about 5.4 KDa to about 7.75 KDa, etc. Furthermore, when "about" and/or "substantially" are/is utilized to describe a value, this is meant to encompass minor variations (up to +/−10%) from the stated value.

While several examples have been described in detail, it is to be understood that the disclosed examples may be modified. Therefore, the foregoing description is to be considered non-limiting.

What is claimed is:

1. An array, comprising:
   a support including a plurality of discrete wells, each of the plurality of discrete wells having a surface opening that is completely surrounded by an interstitial region of the support;
   a gel material positioned in each of the discrete wells;
   sequencing primers grafted to the gel material, the sequencing primers consisting of forward amplification primers and reverse amplification primers; and
   a non-sequencing entity grafted to the gel material, the non-sequencing entity consisting of a dendrimer, polydextran, methacryloyloxyethyl phosphorylcholine, poly(ethylene glycol), poly(ethylene imine), poly-L-lysine, propargyl methacrylate, poly(methyl methacrylate), poly(N-isopropylacrylamide), poly(ethylene glycol) acrylate, poly(propylene imine), poly(vinyl alcohol), poly(2-ethyl-2-oxazoline), polyacrylic acid, poly(trolox ester), a peptide, or a non-functional primer;
each of the sequencing primers and the non-sequencing entity being in its as-grafted form, and wherein the gel material, the sequencing primers, the sequencing primer, and the non-sequencing entity are not present at the interstitial region.

2. The array as defined in claim 1, wherein the non-sequencing entity consists of the non-functional primer, and wherein the non-functional primer is polyT or polyA.

3. The array as defined in claim 1, wherein the non-sequencing entity consists of poly(ethylene glycol) having a molecular weight ranging from about 0.5 KDa to about 10 KDa.

4. The array as defined in claim 1, wherein the non-sequencing entity is grafted to the gel material through a terminal functional group selected from the group consisting of an alkyne, a norbornyl, a copper free click moiety, and a thiol.

5. The array as defined in claim 1, wherein a molar ratio of the non-sequencing entity to the sequencing primers ranges from about 0.25:1 to about 5:1.

6. The array as defined in claim 1, wherein:
the gel material includes a recurring unit of Formula (I):

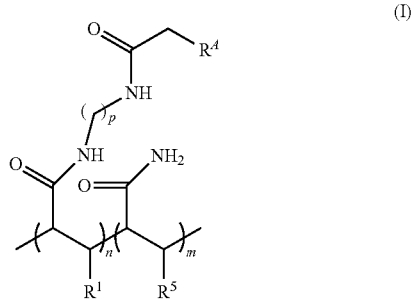

(I)

wherein:
$R^1$ is H or optionally substituted alkyl;
$R^4$ is selected from the group consisting of azido, optionally substituted amino, optionally substituted alkenyl, optionally substituted hydrazone, optionally substituted hydrazine, carboxyl, hydroxy, optionally substituted tetrazole, optionally substituted tetrazine, nitrile oxide, nitrone, and thiol;
$R^5$ is selected from the group consisting of H and optionally substituted alkyl;
each of the —$(CH_2)_p$— can be optionally substituted;
p is an integer in the range of 1 to 50;
n is an integer in the range of 1 to 50,000; and
m is an integer in the range of 1 to 100,000.

7. An array, comprising:
a support including a plurality of discrete wells;
a gel material positioned in each of the discrete wells;
a sequencing primer grafted to the gel material; and
a non-sequencing entity grafted to the gel material;
each of the sequencing primer and the non-sequencing entity being in its as-grafted form and wherein the non-sequencing entity includes a linker and a triplet state quencher or an anti-oxidant bound to the linker.

8. The array as defined in claim 7, wherein:
the linker is selected from the group consisting of a dendrimer, polydextran, methacryloyloxyethyl phosphorylcholine, poly(ethylene glycol), poly(ethylene imine), poly-L-lysine, propargyl methacrylate, poly(methyl methacrylate), poly(N-isopropylacrylamide), poly(ethylene glycol) acrylate, poly(propylene imine), poly(vinyl alcohol), poly(2-ethyl-2-oxazoline), polyacrylic acid, and poly(trolox ester); and
one of:
the triplet state quencher is selected from the group consisting of cyclo-octyltetraene (COT), Trolox (6-hydroxy-2,5,7,8-tetramethylchroman-2-carboxylic acid), and nitrobenzyl alcohol (NBA); and
the anti-oxidant is selected from the group consisting of ascorbate, glutathione, gallic acid, catechin, Trolox (6-hydroxy-2,5,7,8-tetramethylchroman-2-carboxylic acid), and vitamin E.

9. An array, comprising:
a support including a plurality of discrete wells;
a gel material positioned in each of the discrete wells;
a sequencing primer grafted to the gel material; and
a non-sequencing entity grafted to the gel material;
each of the sequencing primer and the non-sequencing entity being in its as-grafted form;
wherein the non-sequencing entity includes a linker and a fluorescence resonance energy transfer (FRET) donor bound to the linker.

10. The array as defined in claim 9, wherein:
the linker is selected from the group consisting of a dendrimer, polydextran, methacryloyloxyethyl phosphorylcholine, poly(ethylene glycol), poly(ethylene imine), poly-L-lysine, propargyl methacrylate, poly(methyl methacrylate), poly(N-isopropylacrylamide), poly(ethylene glycol) acrylate, poly(propylene imine), poly(vinyl alcohol), poly(2-ethyl-2-oxazoline), polyacrylic acid, and poly(trolox ester); and
the FRET donor is selected from the group consisting of a donor dye to FRET with a green-emitting dye and a donor dye to FRET with a red-emitting dye.

11. An array, comprising:
a support including a plurality of discrete wells, each of the plurality of discrete wells having a surface opening that is completely surrounded by an interstitial region of the support;
a gel material positioned in each of the discrete wells;
sequencing primers grafted to the gel material, the sequencing primers consisting of forward amplification primers and reverse amplification primers; and
a spacer grafted to the gel material, the spacer consisting of a dendrimer, polydextran, methacryloyloxyethyl phosphorylcholine, poly(ethylene glycol), poly(ethylene imine), poly-L-lysine, propargyl methacrylate, poly(methyl methacrylate), poly(N-isopropylacrylamide), poly(ethylene glycol) acrylate, poly(propylene imine), poly(vinyl alcohol), poly(-ethyl-2-oxazoline), polyacrylic acid, poly(trolox ester), or combinations thereof, and wherein the gel material, the sequencing primer, and the non-sequencing entities are not present at the interstitial region.

12. The array as defined in claim 11, wherein a molar ratio of the spacer to the sequencing primers ranges from about 0.25:1 to about 5:1.

13. The array as defined in claim 11, wherein the spacer is grafted to the gel material through a terminal functional group selected from the group consisting of an alkyne, a norbornyl, a copper free click moiety, and a thiol.

14. An array, comprising:
a support including a plurality of discrete wells;
a gel material positioned in each of the discrete wells;
a sequencing primer grafted to the gel material;
a spacer grafted to the gel material, the spacer being selected from the group consisting of a dendrimer, polydextran, methacryloyloxyethyl phosphorylcholine, poly(ethylene glycol), poly(ethylene imine), poly-L-lysine, propargyl methacrylate, poly(methyl methacrylate), poly(N-isopropylacrylamide), poly(ethylene glycol) acrylate, poly(propylene imine), poly(vinyl alcohol), poly(-ethyl-2-oxazoline), polyacrylic acid, poly(trolox ester), and combinations thereof; and
a triplet state quencher, an anti-oxidant, or a fluorescence resonance energy transfer (FRET) donor bound to the spacer.

15. The array as defined in claim 14, wherein:
the triplet state quencher is bound to the spacer; and
the triplet state quencher is selected from the group consisting of cyclo-octyltetraene (COT), Trolox (6-hydroxy-2,5,7,8-tetramethylchroman-2-carboxylic acid), and nitrobenzyl alcohol (NBA).

16. The array as defined in claim 14, wherein:
the anti-oxidant is bound to the spacer; and
the anti-oxidant is selected from the group consisting of ascorbate, glutathione, gallic acid, catechin, Trolox (6-hydroxy-2,5,7,8-tetramethylchroman-2-carboxylic acid), and vitamin E.

17. The array as defined in claim 14, wherein:
the FRET donor is bound to the spacer; and
the FRET donor is selected from the group consisting of a donor dye to FRET with a green-emitting dye and a donor dye to FRET with a red-emitting dye.

18. A method, comprising:
positioning a gel material in each of a plurality of discrete wells of a support, each of the plurality of discrete wells having a surface opening that is completely surrounded by an interstitial region of the support;
grafting sequencing primers to the gel material, the sequencing primers consisting of forward amplification primers and reverse amplification primers; and
grafting a non-sequencing entity to the gel material, the non-sequencing entity consisting of a dendrimer, polydextran, methacryloyloxyethyl phosphorylcholine, poly(ethylene glycol), poly(ethylene imine), poly-L-lysine, propargyl methacrylate, poly(methyl methacrylate), poly(N-isopropylacrylamide), poly(ethylene glycol) acrylate, polypropylene imine), poly(vinyl alcohol), poly(2-ethyl-2-oxazoline), polyacrylic acid, poly(trolox ester), a peptide, or a non-functional primer;
wherein each of the sequencing primers and the non-sequencing entity is in its as-grafted form, and wherein the gel material, the sequencing primers, and the non-sequencing entity are not present at the interstitial region.

19. The method as defined in claim 18, wherein the sequencing primers are grafted to the gel material before or after the non-sequencing entity is grafted to the gel material.

20. The method as defined in claim 18, wherein the sequencing primer and the non-sequencing entity are co-grafted to the gel material.

21. The method as defined in claim 20, wherein co-grafting is accomplished by:
depositing a mixture of the sequencing primers and the non-sequencing entity onto the support having the gel material thereon; and
incubating the support at a predetermined temperature.

22. The method as defined in claim 18, wherein:
the non-sequencing entity is grafted to the gel material through a terminal functional group selected from the group consisting of an alkyne, a norbornyl, a copper free click moiety, and a thiol.

23. The method defined in claim 18, wherein:
the gel material includes a recurring unit of Formula (I):

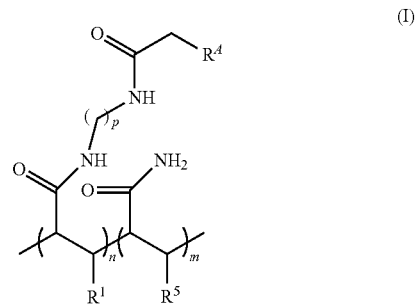

wherein:
$R^1$ is H or optionally substituted alkyl;
$R^A$ is selected from the group consisting of azido, optionally substituted amino, optionally substituted alkenyl, optionally substituted hydrazone, optionally substituted hydrazine, carboxyl, hydroxy, optionally substituted tetrazole, optionally substituted tetrazine, nitrile oxide, nitrone, and thiol;
$R^5$ is selected from the group consisting of H and optionally substituted alkyl;
each of the $-(CH_2)_p-$ can be optionally substituted;
p is an integer in the range of 1 to 50;
n is an integer in the range of 1 to 50,000; and
m is an integer in the range of 1 to 100,000.

* * * * *

UNITED STATES PATENT AND TRADEMARK OFFICE
CERTIFICATE OF CORRECTION

PATENT NO. : 11,466,321 B2
APPLICATION NO. : 16/471411
DATED : October 11, 2022
INVENTOR(S) : James Tsay and Yuxiang Huang It is certified that error appears in the above-identified patent and that said Letters Patent is hereby corrected as shown below:

In the Claims

In Column 25, Lines 10-11, in Claim 1, after "primers," delete "the sequencing primer,".

In Column 26, Line 56, in Claim 11, delete "poly(-ethyl-2-oxazoline)," and insert -- poly(2-ethyl-2-oxazoline), --.

In Column 27, Line 13, in Claim 14, delete "poly(-ethyl-2-oxazoline)," and insert -- poly(2-ethyl-2-oxazoline), --.

In Column 28, Line 9, in Claim 20, delete "sequencing primer" and insert -- sequencing primers --.

In Column 28, Line 22, in Claim 23, after "method" insert -- as --.

Signed and Sealed this
Fourteenth Day of March, 2023

Katherine Kelly Vidal
*Director of the United States Patent and Trademark Office*

SEQUENCE LISTING

```
<160> NUMBER OF SEQ ID NOS: 2

<210> SEQ ID NO 1
<211> LENGTH: 30
<212> TYPE: DNA
<213> ORGANISM: artificial sequence
<220> FEATURE:
<223> OTHER INFORMATION: primer_bind

<400> SEQUENCE: 1
aatgatacgg cgaccaccga gaductacac                                       30

<210> SEQ ID NO 2
<211> LENGTH: 24
<212> TYPE: DNA
<213> ORGANISM: artificial sequence
<220> FEATURE:
<223> OTHER INFORMATION: primer_bind
<220> FEATURE:
<221> NAME/KEY: misc_feature
<222> LOCATION: (22)..(22)
<223> OTHER INFORMATION: 8-oxoguanine

<400> SEQUENCE: 2
caagcagaag acggcatacg anat                                             24
```